(12) United States Patent
Haselby et al.

(10) Patent No.: US 9,175,427 B2
(45) Date of Patent: Nov. 3, 2015

(54) ELECTROSPUN PATTERNED STENT GRAFT COVERING

(75) Inventors: Kenneth A. Haselby, Battle Ground, IN (US); Keith R. Milner, West Lafayette, IN (US); Sara M. Sherman, Lafayette, IN (US); Seoggwan Kim, West Lafayette, IN (US); Richard A. Swift, South Bend, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 329 days.

(21) Appl. No.: 13/295,589

(22) Filed: Nov. 14, 2011

(65) Prior Publication Data
US 2013/0122248 A1 May 16, 2013

(51) Int. Cl.
*B32B 3/24* (2006.01)
*D04H 1/728* (2012.01)
*D01D 5/00* (2006.01)
*A61F 2/07* (2013.01)

(52) U.S. Cl.
CPC ............. *D04H 1/728* (2013.01); *D01D 5/0076* (2013.01); *A61F 2/07* (2013.01); *A61F 2250/0001* (2013.01); *Y10T 428/24273* (2015.01)

(58) Field of Classification Search
CPC ................ D04H 1/728; D01D 5/0076; Y10T 428/24273
USPC ......................................................... 428/131
See application file for complete search history.

(56) References Cited

U.S. PATENT DOCUMENTS

| 3,280,229 A | 10/1966 | Simons |
| 4,130,904 A | 12/1978 | Whalen |
| 4,323,525 A | 4/1982 | Bornat |
| 4,434,797 A | 3/1984 | Silander ......................... 128/343 |
| 4,629,458 A | 12/1986 | Pinchuk |
| 4,657,544 A | 4/1987 | Pinchuk .......................... 623/1 |

(Continued)

FOREIGN PATENT DOCUMENTS

| JP | 2004-313320 | 11/2004 | ............ A61M 29/02 |
| JP | 2006-283241 A | 10/2006 | |

(Continued)

OTHER PUBLICATIONS

Office Action, dated Dec. 13, 2012, pp. 1-20, U.S. Appl. No. 12/959,023, U.S. Patent and Trademark Office, Virginia.

(Continued)

*Primary Examiner* — William P Watkins, III
(74) *Attorney, Agent, or Firm* — Brinks Gilson & Lione (57) ABSTRACT

An endoluminal prosthesis and systems and methods for making the prosthesis are provided. In one example, a patterned graft material for a prosthesis includes a network of electrospun fibers. The network of electrospun fibers may include a plurality of continuous electrospun fibers. The fibers may be collected on a collector plate using an electrospinning process to form the network of fibers. The patterned graft material also may include a plurality of openings in the network of electrospun fibers. The plurality of openings may be arranged in a pattern. The network of electrospun fibers may include a plurality of edges, each surrounding a corresponding one of the plurality of openings. Each of the plurality of edges may include at least one electrospun fiber of the network of electrospun fibers. A majority of the electrospun fibers of the plurality of edges may be continuous at the edges.

8 Claims, 8 Drawing Sheets

(56) References Cited

U.S. PATENT DOCUMENTS

| | | | |
|---|---|---|---|
| 4,689,186 A | 8/1987 | Bornat | |
| 4,759,757 A | 7/1988 | Pinchuk | |
| 4,776,337 A | 10/1988 | Palmaz | 128/343 |
| 5,078,736 A | 1/1992 | Behl | 623/1 |
| 5,628,788 A | 5/1997 | Pinchuk | |
| 5,716,395 A | 2/1998 | Myers et al. | |
| 5,728,150 A | 3/1998 | McDonald et al. | 623/1 |
| 5,769,884 A | 6/1998 | Solovay | |
| 5,866,217 A | 2/1999 | Stenoien et al. | |
| 6,007,573 A | 12/1999 | Wallace et al. | 623/1 |
| 6,110,198 A | 8/2000 | Fogarty et al. | 623/1.12 |
| 6,306,424 B1 | 10/2001 | Vyakarnam et al. | 424/426 |
| 6,334,868 B1 | 1/2002 | Ham | 623/1.13 |
| 6,398,803 B1 | 6/2002 | Layne et al. | |
| 6,537,310 B1 | 3/2003 | Palmaz et al. | 623/1.13 |
| 6,558,414 B2 | 5/2003 | Layne | |
| 6,579,314 B1 | 6/2003 | Lombardi et al. | |
| 6,616,435 B2 | 9/2003 | Lee et al. | 425/83.1 |
| 6,638,621 B2 | 10/2003 | Anderson | 428/402.24 |
| 6,685,956 B2 | 2/2004 | Chu et al. | 424/423 |
| 6,753,311 B2 | 6/2004 | Fertala et al. | 514/2 |
| 6,790,455 B2 | 9/2004 | Chu et al. | 424/423 |
| 6,821,479 B1 | 11/2004 | Smith et al. | 422/1 |
| 6,858,168 B1 | 2/2005 | Vollrath et al. | 264/41 |
| 6,865,810 B2 | 3/2005 | Stinson | 29/896.6 |
| 6,936,298 B2 | 8/2005 | Chaikof et al. | 427/2.24 |
| 6,989,195 B2 | 1/2006 | Anderson | 428/402.24 |
| 7,070,836 B2 | 7/2006 | Czado | 427/462 |
| 7,081,622 B2 | 7/2006 | Kameoka et al. | 250/288 |
| 7,105,229 B2 | 9/2006 | Anderson | 428/402.2 |
| 7,105,810 B2 | 9/2006 | Kameoka et al. | 250/288 |
| 7,112,417 B2 | 9/2006 | Vyakarnam et al. | 435/41 |
| 7,134,857 B2 | 11/2006 | Andrady et al. | 425/66 |
| 7,143,963 B2 | 12/2006 | Tani et al. | 239/456 |
| 7,172,765 B2 | 2/2007 | Chu et al. | 424/423 |
| 7,244,272 B2 | 7/2007 | Dubson et al. | |
| 7,247,338 B2 | 7/2007 | Pui et al. | |
| 7,306,756 B2 | 12/2007 | Edwin et al. | |
| 7,390,524 B1 | 6/2008 | Chen | |
| 7,413,575 B2 | 8/2008 | Phaneuf et al. | |
| 7,591,841 B2 | 9/2009 | Hossainy et al. | |
| 7,704,274 B2 | 4/2010 | Boyle et al. | 623/1.13 |
| 7,736,687 B2 | 6/2010 | Sims et al. | 427/2.1 |
| 7,794,833 B2 | 9/2010 | Balkus, Jr. et al. | 428/364 |
| 7,799,261 B2 | 9/2010 | Orr et al. | 264/441 |
| 7,815,763 B2 | 10/2010 | Fierens et al. | |
| 7,824,601 B1 | 11/2010 | Stankus et al. | |
| 7,854,760 B2 | 12/2010 | Molaei et al. | 623/1.38 |
| 7,922,761 B2 | 4/2011 | Shalev et al. | |
| 7,947,069 B2 | 5/2011 | Sanders | |
| 8,057,535 B2 | 11/2011 | Hashi et al. | |
| 8,100,683 B2 | 1/2012 | Orr et al. | 425/174.8 R |
| 8,123,794 B2 | 2/2012 | Flagle et al. | |
| 8,157,857 B2 | 4/2012 | Case et al. | |
| 8,178,030 B2 | 5/2012 | Anneaux et al. | |
| 8,257,640 B2 | 9/2012 | Anneaux et al. | |
| 8,262,979 B2 | 9/2012 | Anneaux et al. | |
| 2003/0100944 A1 | 5/2003 | Laksin et al. | 623/1.44 |
| 2003/0109917 A1 | 6/2003 | Rudin et al. | |
| 2003/0195611 A1 | 10/2003 | Greenhalgh et al. | |
| 2003/0211135 A1 | 11/2003 | Greenhalgh et al. | |
| 2004/0018226 A1 | 1/2004 | Wnek et al. | 424/443 |
| 2004/0030377 A1 | 2/2004 | Dubson et al. | |
| 2004/0037813 A1 | 2/2004 | Simpson et al. | 424/93.7 |
| 2004/0051201 A1 | 3/2004 | Greenhalgh et al. | |
| 2004/0116997 A1 | 6/2004 | Taylor et al. | 623/1.11 |
| 2004/0241436 A1 | 12/2004 | Hsieh et al. | 428/361 |
| 2005/0064168 A1 | 3/2005 | Dvorsky et al. | 428/292.1 |
| 2005/0104258 A1 | 5/2005 | Lennhoff | |
| 2005/0137680 A1 | 6/2005 | Ortiz et al. | |
| 2006/0048355 A1 | 3/2006 | Kim | 28/104 |
| 2006/0085063 A1 | 4/2006 | Shastri et al. | 623/1.41 |
| 2006/0195142 A1 | 8/2006 | Shalaby | 606/228 |
| 2006/0200232 A1 | 9/2006 | Phaneuf et al. | 623/1.42 |
| 2006/0213829 A1 | 9/2006 | Rutledge et al. | 210/503 |
| 2006/0259131 A1 | 11/2006 | Molaei et al. | |
| 2006/0264140 A1 | 11/2006 | Andrady et al. | |
| 2007/0031607 A1 | 2/2007 | Dubson et al. | 427/458 |
| 2007/0043428 A1 | 2/2007 | Jennings et al. | 623/1.15 |
| 2007/0087027 A1 | 4/2007 | Greenhalgh et al. | 424/423 |
| 2007/0162110 A1 | 7/2007 | Dave | 623/1.42 |
| 2008/0027531 A1 | 1/2008 | Reneker et al. | |
| 2008/0200975 A1 | 8/2008 | Dubson | |
| 2008/0208325 A1 | 8/2008 | Helmus et al. | |
| 2008/0241352 A1 | 10/2008 | Shalaby | |
| 2009/0069904 A1 | 3/2009 | Picha | 623/23.72 |
| 2009/0112306 A1 | 4/2009 | Bonsignore et al. | |
| 2009/0138070 A1 | 5/2009 | Holzer et al. | |
| 2009/0227026 A1 | 9/2009 | Rapoport et al. | |
| 2009/0248131 A1 | 10/2009 | Greenan | |
| 2010/0179644 A1 | 7/2010 | Jennings et al. | |
| 2010/0222771 A1 | 9/2010 | Mitchell et al. | |
| 2010/0241214 A1 | 9/2010 | Holzer et al. | |
| 2010/0318193 A1 | 12/2010 | Desai et al. | |
| 2011/0009949 A1 | 1/2011 | Stankus et al. | |
| 2011/0022149 A1 | 1/2011 | Cox et al. | |
| 2011/0022159 A1 | 1/2011 | Fierens et al. | 623/1.39 |
| 2011/0135806 A1 | 6/2011 | Grewe et al. | 427/2.25 |
| 2011/0262684 A1 | 10/2011 | Wintsch et al. | |
| 2011/0301696 A1 | 12/2011 | Mangiardi | |
| 2012/0141656 A1 | 6/2012 | Orr et al. | |
| 2013/0018220 A1 | 1/2013 | Vad et al. | |

FOREIGN PATENT DOCUMENTS

| | | | |
|---|---|---|---|
| JP | 2007-303021 | 11/2007 | |
| WO | WO 03/072287 A1 | 9/2003 | B23H 11/00 |
| WO | WO 2010/112564 A1 | 10/2010 | |
| WO | WO 2012/006072 A2 | 1/2012 | |

OTHER PUBLICATIONS

Search Report for European Patent Application Serial No. 12192656.2, dated Feb. 19, 2013, pp. 1-8.

Salim et al., "Selective Nanofiber Deposition Via Electrodynamic Focusing", *Nanotechnology*, vol. 19, 2008, pp. 1-8.

ELECTROSPUN PATTERNED STENT GRAFT COVERING

TECHNICAL FIELD

This disclosure relates to endoluminal medical devices for implantation within the human or animal body for treatment of endovascular disease. More particularly, it relates to an endoluminal prosthesis having a patterned graft material and methods of manufacturing such an endoluminal prosthesis.

BACKGROUND

Covered stents, or stent grafts, have been used to treat a variety of medical conditions, including aneurysms, occluded vessels, and restenosis. Various materials and methods have been used to create coverings, or grafts, that may be applied to stents to form stent grafts. Typically, stent grafts are designed to be substantially nonporous. These nonporous stent grafts may be designed to prevent the flow of blood through the graft material (such as a stent graft for excluding an aneurysm) or to limit or control cellular in-growth to prevent restenosis. In fact, stent grafts produced using porous graft materials often may be "pre-clotted" to reduce the permeability of the graft material prior to implanting the stent graft within a patient's body.

Some stent grafts have been designed to have some degree of porosity. These grafts may be manufactured to have a specific pattern or configuration designed to achieve a desired result such as promoting or diminishing endothelial growth or controlling the permeability of fluids through the grafts. The patterns may be generated by processes such as weaving, extrusion, laser marking, and mechanical punching. Typically, additional manufacturing steps are required to generate a pattern on a graft after the graft itself has been produced.

Electrospinning is a process for creating a non-woven network of fibers using an electrically charged solution that is driven from a source to a target with an electrical field. More specifically, a solution is driven from an orifice, such as a needle. A voltage is applied to the orifice resulting in a charged solution jet or stream from the orifice to the target. The jet forms a conical shape, termed a Taylor cone, as it travels from the orifice. As the distance from the orifice increases, the cone becomes stretched until the jet splits or splays into many fibers prior to reaching the target. The fibers are extremely thin, typically in the nanometer range. The collection of fibers on the target forms a thin mesh layer of fibrous material.

It may be desirable to provide a patterned graft material in a single manufacturing step. It also may desirable to use an electrospinning process to form a patterned graft material having a precisely controlled porosity.

SUMMARY

The present embodiments provide an endoluminal prosthesis having a patterned graft material and methods of manufacturing such an endoluminal prosthesis.

In one example, a patterned graft material for a prosthesis includes a network of electrospun fibers. The network of electrospun fibers may include a plurality of continuous electrospun fibers. The patterned graft material also may include a plurality of openings in the network of electrospun fibers. The plurality of openings may be arranged in a pattern. The network of electrospun fibers may include a plurality of edges, each surrounding a corresponding one of the plurality of openings. Each of the plurality of edges may include at least one electrospun fiber of the network of electrospun fibers. A majority of the electrospun fibers of the plurality of edges may be continuous at the edges.

In another example, a method of making a patterned graft material for a prosthesis may include providing a spinneret and a collector plate. The collector plate may include a plurality of openings arranged in a pattern. The method may include dispensing a solution from an orifice of the spinneret to generate a plurality of fibers. The method also may include collecting the plurality of fibers on the collector plate to form a coating of non-woven fibers. The formed coating may include a plurality of openings corresponding to the plurality of openings in the collector plate.

In yet another example, an electrospinning apparatus for making a patterned graft material for a prosthesis may include a spinneret and a collector plate. The collector plate may include a plurality of openings arranged in a pattern. The patterned graft material may include a plurality of openings corresponding to the plurality of openings in the collector plate.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

DETAILED DESCRIPTION OF THE DRAWINGS AND THE PRESENTLY PREFERRED EMBODIMENTS

The present disclosure relates to an endoluminal prosthesis having a patterned graft material and methods of manufacturing such an endoluminal prosthesis.

In the present disclosure, the term "proximal" refers to a direction that is generally closest to the heart during a medical procedure, while the term "distal" refers to a direction that is farthest from the heart during a medical procedure.

Figure 1:
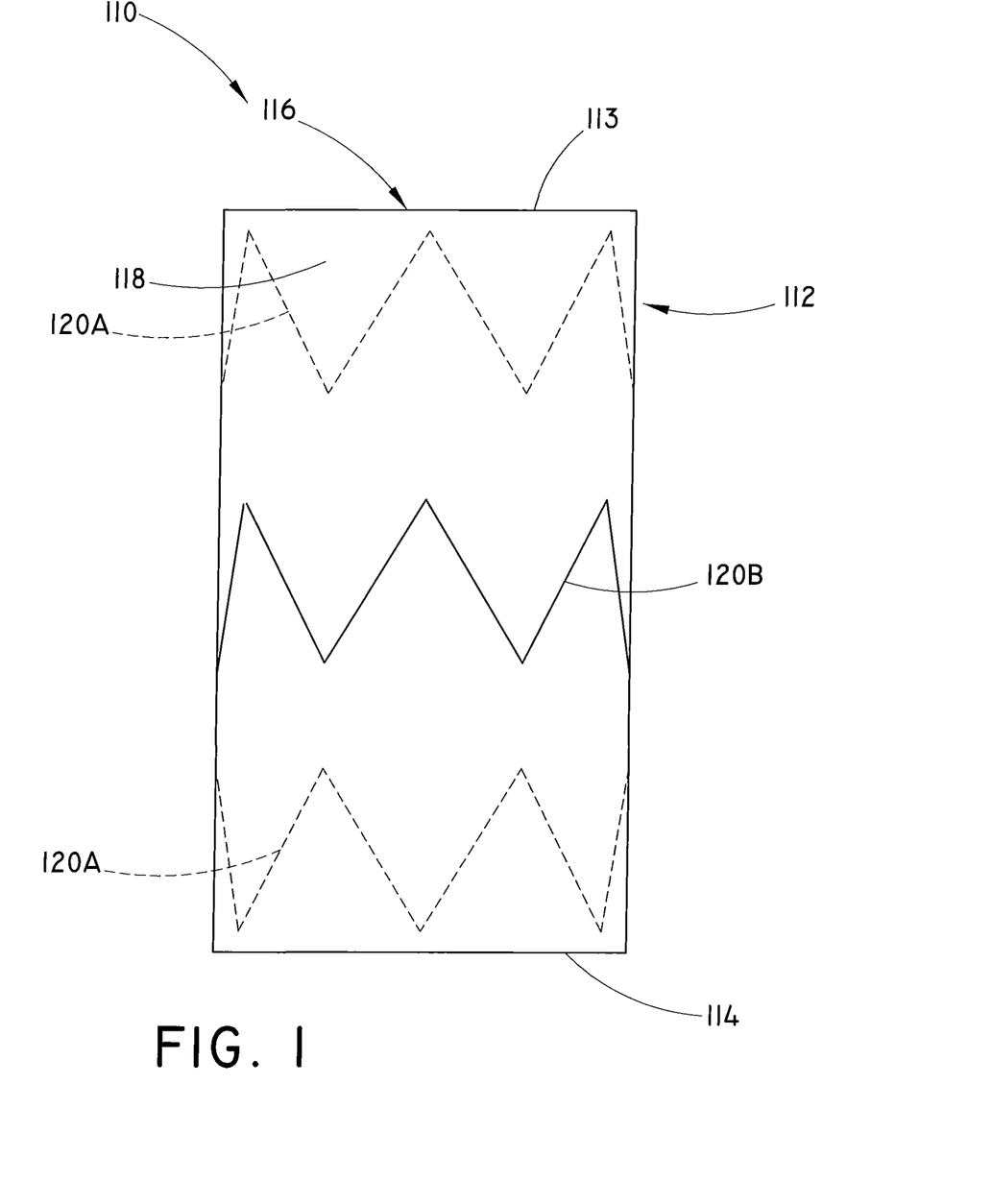
FIG. 1 illustrates one example of a prosthesis.

FIG. 1 depicts one example of an endoluminal prosthesis 110. In this example, the prosthesis 110 is a stent graft. The prosthesis 110 may include a graft body 112. The graft body 112 may be configured as a tubular body having a generally cylindrical shape. The graft body 112 may have a proximal end 113, a distal end 114, and a lumen 116 extending longitudinally between the proximal and distal ends thereof. The lumen 116 may be configured to permit blood or other body fluids to flow between the proximal end 113 and distal end 114 of the graft body 112.

The graft body 112 may be formed of a graft material 118. The graft material 118 may be formed as a sheet of biocompatible material. The sheet of biocompatible material may be formed as a generally planar sheet that may be rolled or otherwise formed into a tube to form the graft body 112. A seam may be formed in the surface of the graft body 112 where opposing edges of the sheet are joined to one another to form the graft body. Alternatively, the sheet may be formed in the tubular shape of the graft body 112 such that the graft body may be seamless.

Many different types of biocompatible materials may be used to form the graft material 118 of the graft body 112. The biocompatible material may be substantially non-toxic in the in vivo environment of its intended use, and may be substantially unrejected by the patient's physiological system (i.e., may be non-antigenic). Examples of biocompatible materials from which textile graft material can be formed include, for example, polyesters, such as polyethylene terephthalate; fluorinated polymers, such as polytetrafluoroethylene (PTFE) and fibers of expanded PTFE, polyvinylidene fluoride (PVFD), and polyurethanes. In addition, materials that are not inherently biocompatible may be subjected to surface modifications to render the materials biocompatible. Examples of surface modifications include, for example, graft polymerization of biocompatible polymers on the surface, coating of the surface with a crosslinked biocompatible polymer, chemical modification with biocompatible functional groups, and immobilization of a compatibilizing agent such as heparin or other biocompatible substances. Thus, any fibrous material having sufficient strength to survive in the in vivo environment may be used to form the graft material, provided the final material is biocompatible. In addition to the polyesters, fluorinated polymers, and polyurethanes listed above, fibers suitable for making graft materials include polyethylene, polypropylene, polyvinyl chloride (PVC), polyaramids, polyacrylonitrile, nylon, silicone, and cellulose. Bioremodelable materials also may be used singly or in combination with the aforementioned polymer materials.

The graft material may be made of one or more polymers that do not require treatment or modification to be biocompatible. The graft body may be constructed from woven multifilament polyester such as, for example, Dacron™, commercially available from DuPont, Wilmington, Del. The graft material also may be made from natural or organic materials. For example, the graft material may be made from a biological scaffold or bioremodelable material such as small intestine submucosa ("SIS"), commercially available from Cook Biotech, West Lafayette, Ind. The graft material also may be made from biodegradable materials such as polylactides. The graft body may be formed from a single layer or multiple layers of graft material. In embodiments employing a plurality of layers of material, the layers may remain separate, or may be attached to one another through a secondary process such as sintering, curing, adhesives, sutures, or the like.

The prosthesis 110 also may include at least one stent 120. The stent 120 may be coupled to the graft body 112. In the example of FIG. 1, a plurality of internal stents 120a are coupled to an inner surface of the graft body 112, and an external stent 120b is coupled to an outer surface of the graft body. While one exemplary arrangement is shown in FIG. 1, it will be appreciated by one of ordinary skill in the art that each of the stents 120 may be coupled to inner and/or outer surfaces of the graft body 112. An internal stent 120a may be a sealing stent and may be placed at or near the proximal end 113 of the graft body 112 to seal the proximal end of the graft body against the wall of a blood vessel into which the prosthesis 110 is placed. Additionally, or alternatively, depending on the location where the prosthesis 110 is placed or a particular need, a sealing stent may be placed at either or both of the proximal end 113 and distal end 114 of the graft body 112.

Stents may add rigidity, expansion force, and/or support to the prosthesis. A stent may be used to obtain and maintain the patency of a body passageway while maintaining the integrity of the passageway. The stents may be made from one or more of numerous metals and/or alloys. For example, the stents may be made from a metallic material such as stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide ($Li_2O_3$), and a nickel-titanium alloy, such as nitinol, or other suitable materials known in the art. In one example, the stents may include a shape-memory material such as nitinol. Moreover, the stents may be configured in any of a variety of structures to provide a suitable intraluminal support structure. For example, one or more stents may be made from a woven wire structure, a laser-cut cannula, individual interconnected rings, or another pattern or design.

In one example, shown in FIG. 1, the stents 120 may be configured in the form of one or more "Z-stents" or Gianturco stents, each of which may include a series of substantially straight segments interconnected by a series of bent segments. The bent segments may include acute bends or apices. The Gianturco stents are arranged in a zigzag configuration in which the straight segments are set at angles relative to one another and are connected by the bent segments. However, as noted above, the stents may be configured in any suitable configuration, and one or more stents may be provided.

Although the discussion in this disclosure will refer to the prosthesis 110, a person having ordinary skill in the art will recognize that the devices and methods described herein may be equally applicable to a prosthesis, such as a stent or stent graft, having any other configuration. For example, the prosthesis may be configured as a bifurcated stent graft, a stent graft having branches, scallops and/or fenestrations, or a prosthesis having any other shape or features. Such devices and methods are contemplated by and within the scope of this disclosure.

Figure 2:
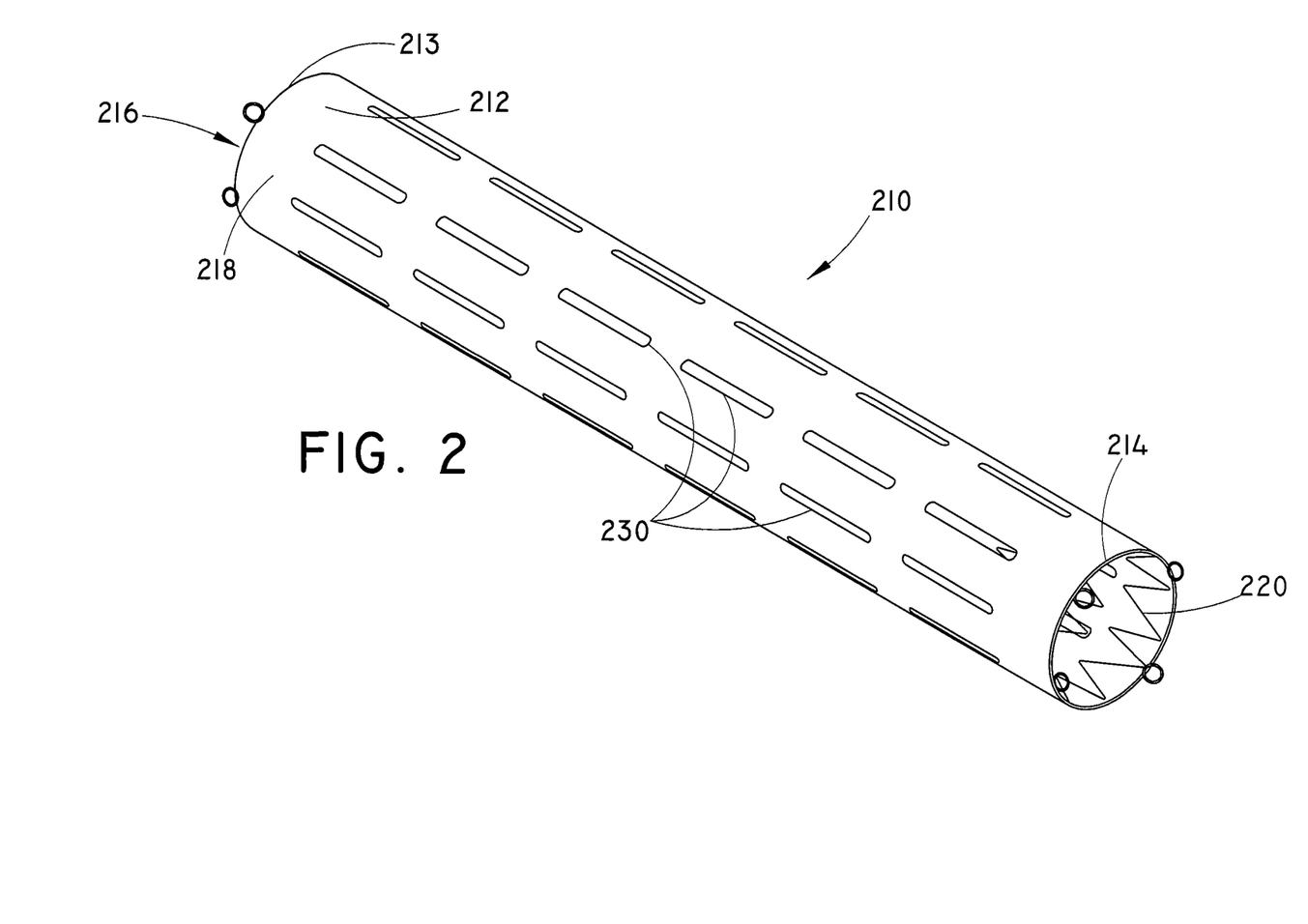
FIG. 2 is a perspective view of one example of a prosthesis having a patterned graft material.

FIG. 2 depicts another example of a prosthesis 210. The prosthesis 210 may be similar to the prosthesis 110 of FIG. 1 in many respects. For example, the prosthesis 210 may include a graft body 212 formed of a graft material 218. The graft body 212 may have a proximal end 213, a distal end 214, and a lumen 216 extending longitudinally therein. A plurality of stents 220 may be disposed along the graft body 212.

As shown in FIG. 2, the prosthesis 210 also may include a plurality of openings 230. Each opening 230 of the plurality of openings may be formed through the graft material 218 of the prosthesis 210. In other words, each opening 230 may extend entirely through the graft material from the inner surface of the graft body 212 to the outer surface of the graft body. The lumen 216 of the prosthesis 210 may be in fluid communication with a region external to the prosthesis via the openings 230. The openings 230 may provide the graft material 218 of the graft body 212 with a determined porosity. In other words, the openings 230 may enable a controlled amount of blood or other body fluid to permeate the graft material 218. The porosity of the graft material (and thus the amount of blood or other body fluid that may be allowed to flow therethrough) may be controlled as further described below. The openings 230 may have any one of a variety of geometries including circular, semi-circular, oval, oblong, or other geometries.

A porous graft material may be made using any type of process. For example, openings may be formed through a substantially nonporous graft material by processes such as laser marking and mechanical punching. In another example, a porous graft material may be formed by processes such as weaving or extrusion. In yet another example, a porous graft material may be formed by an electrospinning process. One type of electrospinning process is described in U.S. Pat. No. 7,799,261 to Orr et al., which is incorporated herein by reference.

There may be a variety of situations in which it may be desirable to provide a prosthesis having a porous graft material. For example, a prosthesis having a porous graft material may be deployed to treat an aneurysm within a body vessel of a patient. A sufficient amount of blood may be allowed to permeate the graft material and flow into the aneurysmal portion of the vessel to encourage embolization within the aneurysmal sac. In another example, a prosthesis having a porous graft material may be implanted in a portion of a body vessel having both diseased and non-diseased regions. A sufficient amount of blood may be allowed to flow through the graft material to provide blood flow to the non-diseased regions of the vasculature that may be covered by the prosthesis. In yet another example, a prosthesis having a porous graft material may be implanted in a body vessel in such a position that the prosthesis may overlap or cover the ostium of one or more branching vessels. A sufficient amount of blood may be allowed to flow through the graft material to maintain blood flow into the branching vessels.

Figure 3:
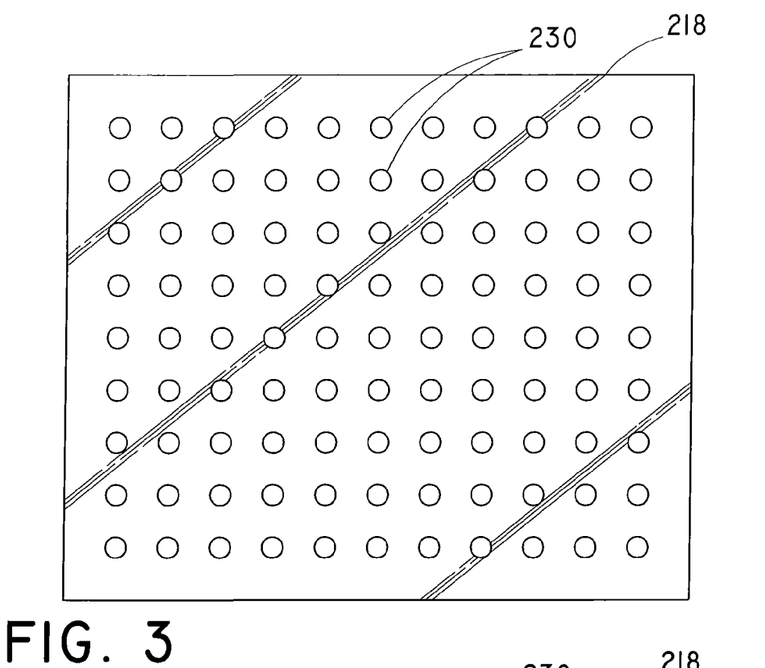
FIG. 3 illustrates one example of a patterned graft material.
Figure 4:
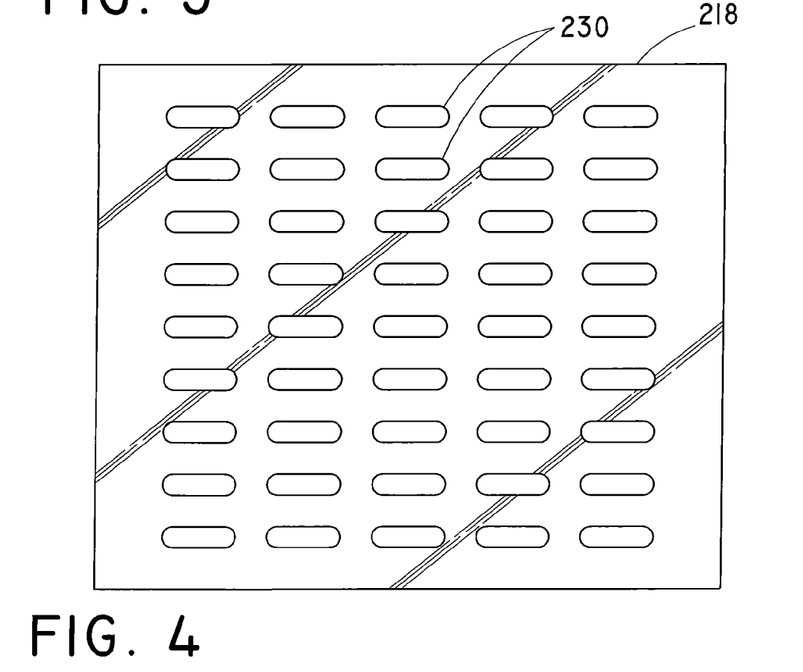
FIG. 4 illustrates one example of a patterned graft material.
Figure 5:
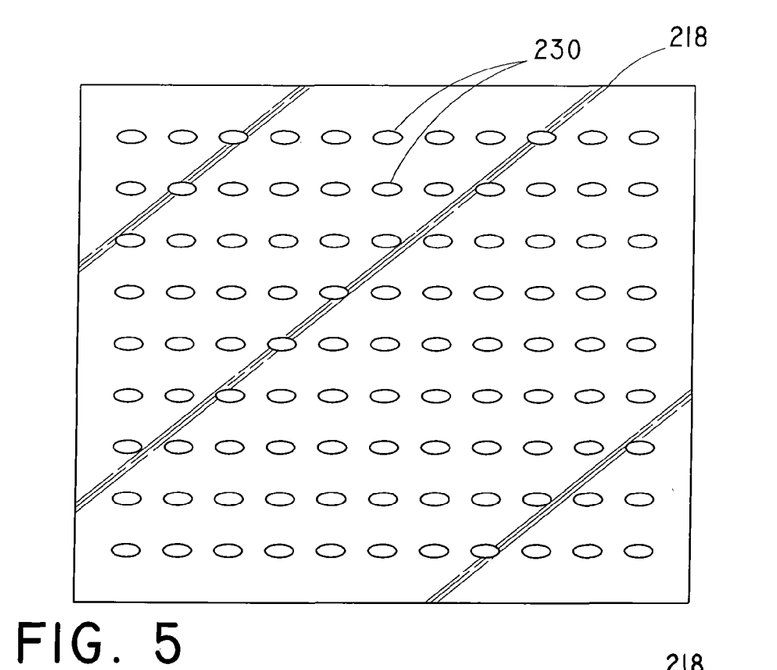
FIG. 5 illustrates one example of a patterned graft material.
Figure 6:
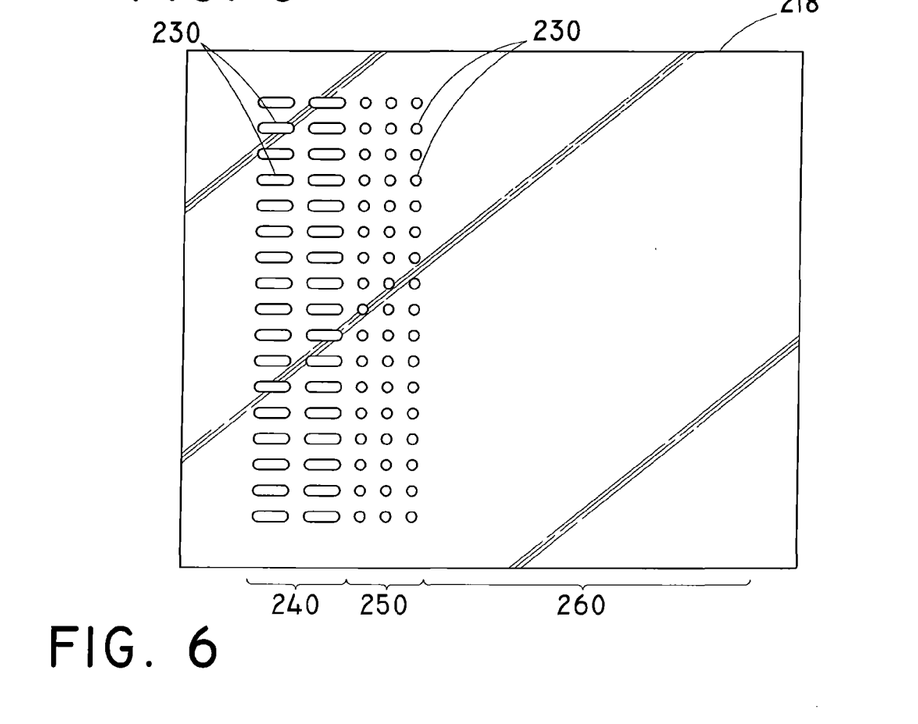
FIG. 6 illustrates one example of a patterned graft material.

FIGS. 3-6 depict different examples of graft materials having a plurality of openings. FIG. 3 illustrates one example of a graft material that may include a plurality of substantially circular openings arranged in a grid or array on the graft material. FIG. 4 illustrates another example of a graft material that may include a plurality of openings configured as elongated slots. The slots may be arranged in a grid or array on the graft material. FIG. 5 illustrates yet another example of a graft material that may include a plurality of substantially elliptical openings arranged in a grid or array on the graft material. FIG. 6 illustrates yet another example of a graft material that may include a plurality of openings configured as elongated slots and another plurality of substantially elliptical openings. The slots may be arranged in a grid or array on a region of the graft material, and the elliptical openings may be arranged in another grid or array on another region of the graft material. Yet another region of the graft material may be substantially free of openings as further described below.

The plurality of openings 230 of the prosthesis 210 may include any number of openings. The openings 230 may be configured to have any shape including, for example, circular, elliptical, rectangular, and any other polygonal or non-polygonal shape. The openings 230 also may be configured to have any size. The openings 230 may be sized to form a graft material having a desired porosity. For example, larger openings may be provided to form a graft material having a greater porosity, and smaller openings may be provided to form a graft material having a lower porosity. The openings 230 also may be shaped to form a graft material having a desired porosity. For example, a generally circular opening may pass a different amount of blood than a generally elliptical opening or a generally rectangular opening having a similar size. Such differences may be caused by different flow characteristics of blood through openings of different shapes. The number of openings and/or the size and shape of each opening may be selected to provide a graft material having a determined porosity. In one non-limiting example, the determined porosity may be about 70%. Each opening 230 of the plurality of openings may have the same size and shape as shown in FIGS. 3-5. Alternatively, the plurality of openings 230 may include openings having different sizes and/or shapes as shown in FIG. 6.

The plurality of openings 230 of the prosthesis 210 also may be arranged in any pattern. For example, FIGS. 3-6 illustrate four potential patterns in which the plurality of openings 230 may be arranged. The openings 230 may be arranged in a desired uniform pattern with respect to the graft material 218. For example, the openings 230 may be arranged in a grid pattern as shown in FIGS. 3-5. In one example, the grid pattern may include a plurality of substantially circular openings as shown in FIG. 3. In another example, the grid pattern may include a plurality of elongate slots as shown in FIG. 4. The slots may be arranged such that, upon forming the graft material into a tubular prosthesis, the long axes of the slots are aligned with the longitudinal axis of the prosthesis. Alternatively, the slots may be arranged such that, upon forming the graft material into a tubular prosthesis, the long axes of the slots are aligned with the circumference of the prosthesis. In yet another example, the grid pattern may include a plurality of substantially elliptical openings as shown in FIG. 5. The openings may be arranged such that, upon forming the graft material into a tubular prosthesis, the long axes of the ellipses are aligned with the longitudinal axis of the prosthesis. Alternatively, the openings may be arranged such that, upon forming the graft material into a tubular prosthesis, the long axes of the ellipses are aligned with the circumference of the prosthesis. Alternatively, the openings 230 may be arranged in a non-uniform pattern with respect to the graft material 218. For example, one region of the graft material 218 may have a greater concentration of openings 230 than another region of the graft material as shown in FIG. 6. In this example, the grid pattern may include a plurality of elongate slots and a plurality of substantially elliptical openings. The slots may be arranged such that, upon forming the graft material into a tubular prosthesis, the long axes of the slots are aligned with the longitudinal axis of the prosthesis. Alternatively, the slots may be arranged such that, upon forming the graft material into a tubular prosthesis, the long axes of the slots are aligned with the circumference of the prosthesis. Similarly, the openings may be arranged such that, upon forming the graft material into a tubular prosthesis, the long axes of the ellipses are aligned with the longitudinal axis of the prosthesis. Alternatively, the openings may be arranged such that, upon forming the graft material into a tubular prosthesis, the long axes of the ellipses are aligned with the circumference of the prosthesis.

The openings 230 may be arranged in a pattern such that the porosity of the graft material 218 may vary along a length of the prosthesis 210. For example, the graft material may have a pattern of openings including three regions along a length of the graft material as shown in FIG. 6. A first region 240 may have a first porosity produced by a first pattern of openings, a second region 250 may have a second porosity produced by a second pattern of openings, and a third region 260 may be substantially non-porous (i.e., may not include any openings). In this manner, the graft material may be configured such that different amounts of blood may be allowed to permeate the graft material through each of the three regions thereof. As will be recognized by one of ordinary skill in the art, any number of regions may be provided, each region having a determined porosity. The openings also may be arranged in a pattern such that the porosity of the graft material may vary along a width or circumference of the prosthesis in similar fashion.

Such variable porosity may be beneficial in a variety of situations. In one example, a prosthesis may be used to treat an aneurysm of the abdominal aorta. It may be desirable to position the prosthesis such that a portion of the prosthesis may cover the ostium of one or more branching vessels of the aorta. For example, it may be desirable to position the prosthesis such that a portion of the prosthesis extends over the ostia of the renal arteries so that the prosthesis may be anchored in a healthy region of the aorta. A pattern of openings may be provided in the region of the prosthesis covering the ostia of the renal arteries. Blood may be allowed to permeate that portion of the prosthesis having the openings to supply blood to the renal arteries. The remainder of the prosthesis may be substantially nonporous to prevent blood flow into the aneurysmal sac.

Figure 7:
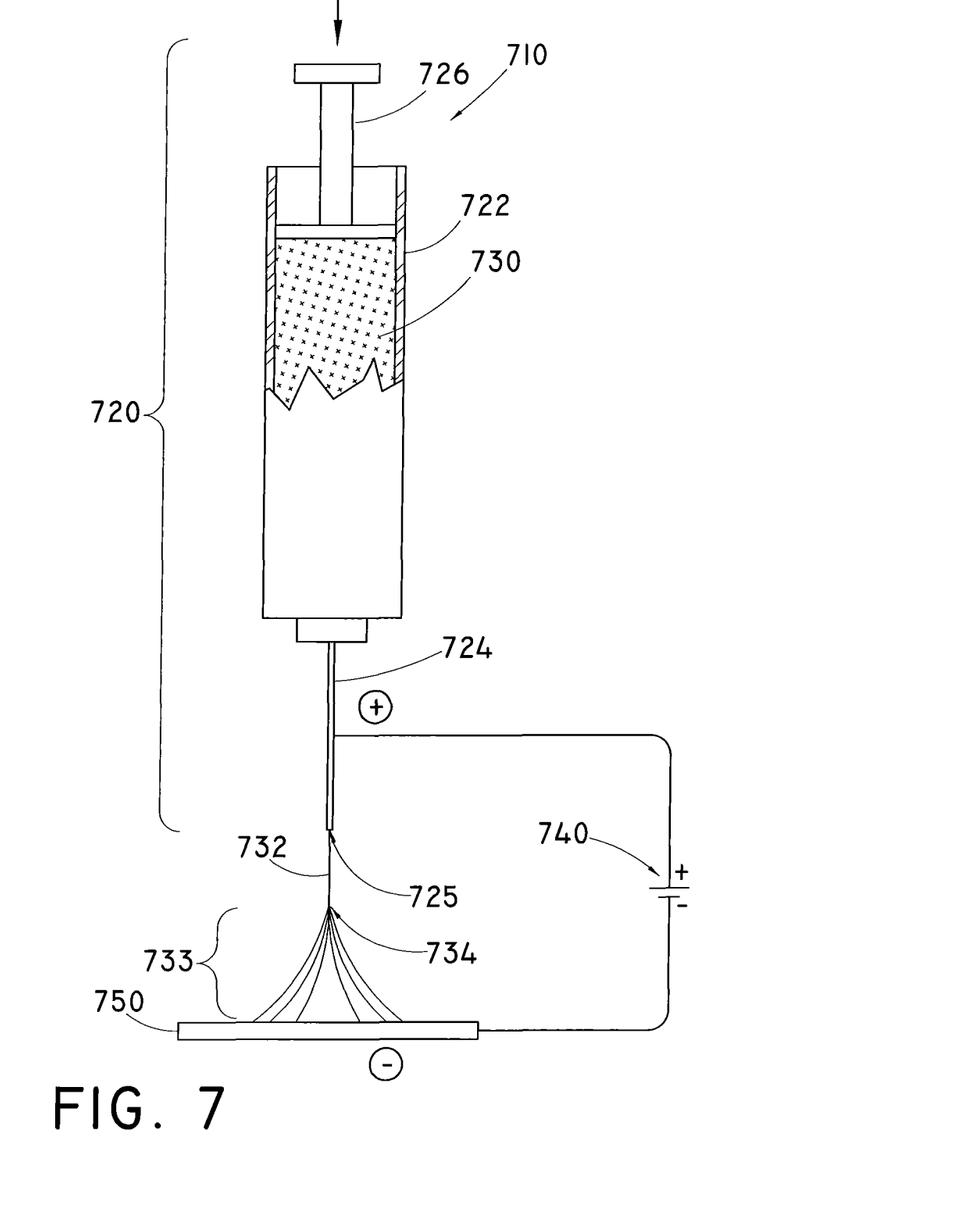
FIG. 7 illustrates one example of an electrospinning apparatus for making a patterned graft material.

A porous graft material may be formed by an electrospinning process. One type of electrospinning process is described in U.S. Pat. No. 7,799,261 to Orr et al., which is incorporated herein by reference. FIG. 7 depicts one example of an electrospinning apparatus 710 that may be used to make a graft material as described herein. The electrospinning process will be described in reference to the electrospinning apparatus 710. The electrospinning apparatus 710 may include a spinneret 720. The spinneret 720 may include a reservoir 722. The reservoir 722 may be configured as a syringe-like container as shown in FIG. 7. The reservoir 722 may be fluidly coupled to an orifice 724 to form the spinneret 720. The orifice 724 may be configured as a needle as shown in FIG. 7.

A solution 730 may be loaded into the reservoir 722. Suitable solutions will be discussed in more detail below. The orifice 724 may have a distal opening 725 through which the solution 730 may be driven by a displacement system 726. The displacement system 726 may be configured as any type of controllable, variable rate fluid displacement system. For example, the fluid displacement system 726 may be configured as a plunger as shown in FIG. 7. Preferably, the displacement system 726 may be an automated system to provide a consistent and accurate flow of solution 730 through the orifice 724. In one example, the fluid displacement system 726 may deliver the solution 730 at a delivery rate of about 0 mL/hr to about 25 mL/hr, about 1 mL/hr to about 10 mL/hr, or about 3 mL/hr to about 7 mL/hr.

A voltage source 740 may generate an electric potential across the spinneret 720 and a collector plate 750. In one example, the electric potential may be between about 10 kV and about 35 kV, between about 15 kV and about 30 kV, or between about 20 kV and about 25 kV. The electric potential 740 may aid the displacement system 726 in ejecting the solution 730 from the distal opening 725 of the orifice 724.

The solution may form a charged jet or stream 732 from the distal opening 725 to the collector plate 750. The solution stream 732 may form a conical shape 733, called a Taylor cone, between the spinneret 720 and the collector plate 750. As the solution stream 732 travels away from the opening 725, the cone 733 may begin to splay or stretch at a position 734 between the spinneret 720 and the collector plate 750. In one example, the distance between the distal opening 725 and the collector plate 750 may be between about 0.1 inches to about 6 inches, between about 0.5 inches to about 4 inches, or between about 1 inch to about 2 inches. Position 734 need not be substantially intermediate the distal opening 725 and the collector plate 750, and may be located at any desired distance between the distal opening and the collector plate. The splaying or stretching action may create a plurality of fibers that may or may not dry upon reaching the collector plate 750, depending on the volatility of the chosen solvent. The fibers may contact the collector plate 750 to form a coating of non-woven fibers thereon. The coating of non-woven fibers may be configured as a network of fibers deposited on the collector plate to collectively form a sheet.

The collector plate 750 may be formed from any conductive material known in the art. In one example, the collector plate 750 may be formed from a metallic material such as stainless steel (e.g., electropolished stainless steel) or chrome. In another example, the collector plate 750 may be formed from a non-metallic material such as a conductive plastic material. The collector plate 750 may be sized and shaped to correspond to a desired size and shape of a graft material for covering a prosthesis such as a stent graft. In one example, the collector plate 750 may be configured as a substantially flat, planar plate. The collector plate 750 may have a length corresponding to a length of the prosthesis and a width corresponding to a circumference of the prosthesis. The coating or network of non-woven fibers formed on the collector plate 750 during the electrospinning process may be removed from the collector plate and rolled into a tube to form the graft body of the prosthesis as described above. In another example, the collector plate 750 may be configured as a generally cylindrical tubular member. The collector plate 750 may have a length corresponding to the length of the prosthesis and a circumference corresponding to the circumference of the prosthesis. The tubular coating or network of non-woven fibers formed on the collector plate 750 during the electrospinning process may be removed from the collector plate for use as the graft body of the prosthesis as described above. In this example, the resulting graft material may provide a seamless graft body also as described above. A release layer may be applied to the surface of the collector plate 750 on which the coating of non-woven fibers is formed. The release layer may aid in removing the coating of non-woven fibers from the collector plate in a single piece and undamaged for use as the graft material of the prosthesis. The release layer may be formed of any material known in the art. Preferably, the release layer may be formed of a non-stick material such as, for example, PTFE, sodium bicarbonate, a silicone lubricant, or any other biocompatible lubricant.

A plurality of openings may be formed in the collector plate 750. The plurality of openings may be arranged in a pattern. The pattern may have any type of configuration including those described above with respect to FIGS. 3-6. The coating of non-woven fibers formed on the collector plate 750 during the electrospinning process may include a plurality of openings corresponding to the openings formed in the collector plate. In other words, the fibers generated during the electrospinning process may contact only the solid portions of the collector plate (and not the openings formed in the collector plate) to form a coating of non-woven fibers having a plurality of openings corresponding to the plurality of openings formed in the collector plate. In this manner, the electrospinning process may be used to form a graft material having a plurality of openings as described above. The openings formed in the collector plate may be sized, shaped, and/or arranged to provide a graft material having a determined porosity. The openings also may be sized, shaped, and/or arranged to form a graft material having different regions with varying porosities as described above.

Figure 8:
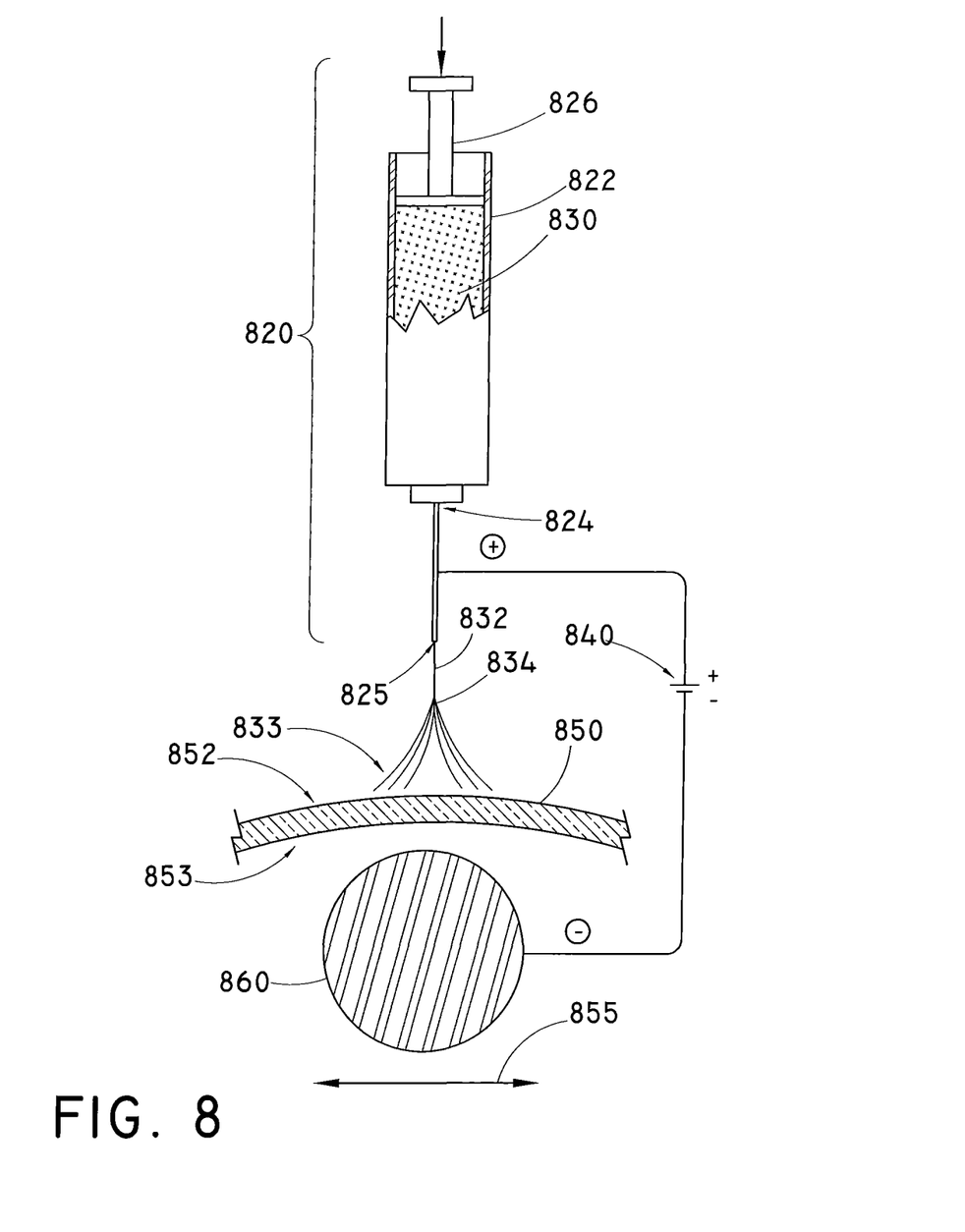
FIG. 8 illustrates one example of an electrospinning apparatus for making a patterned graft material.

FIG. 8 depicts another example of an electrospinning apparatus 810 that may be used to make a graft material as described herein. A portion of a collector plate 850 may be placed between a spinneret 820 and a target 860. The collector plate 850 may include a first surface 852 and an opposing second surface 853. The target 860 may be located adjacent the second surface 853 of the collector plate 850. The spinneret 820 may include a reservoir 822 that may be fluidly coupled to an orifice 824. A solution 830 may be loaded into the reservoir 822. The orifice 824 may have a distal opening 825 through which the solution 830 may be driven by a displacement system 826. The distal opening 825 may be oriented in the direction of the collector plate 850. For example, the distal opening 825 may be oriented toward the target 860 such that any solution 830 that exits the distal opening may be directed toward the collector plate 850.

A voltage source 840 may generate an electric potential across the spinneret 820 and the target 860. The displacement system 826 may be advanced distally relative to the reservoir 822 to urge the solution 830 from the spinneret 820. The electric potential and the movement of the displacement system 826 may eject the solution 830 from the spinneret 820. The solution 830 may exit the distal opening 825 as a charged jet or stream 832. The stream 832 may be directed toward the first surface 852 of the collector plate 850, for example, by the charged target 860. The solution stream 832 may form a cone 833. As the solution stream 832 travels from the opening 825 toward the collector plate 850, the cone 833 may splay at a position 834 between the spinneret 820 and the collector plate 850. The splaying or stretching action may create a plurality of fibers, such as nanofibers. The fibers may contact the first surface 852 of the collector plate 850 to form a coating of non-woven fibers thereon.

The collector plate 850 may be moved relative to the spinneret 820 and/or the target 860. Such movement may enable the coating of any portion of the first surface 852 of the collector plate 850. For example, the first surface 852 may be coated almost entirely, partially, or at discrete locations thereon. For example, the collector plate 850 may be moved in a first direction 855 along an x-axis to direct the fibers about a width of the first surface 852 of the collector plate. The collector plate 850 also may be moved in a second direction perpendicular to the first direction along a y-axis to direct the fibers about a length of the first surface 852 of the collector plate. Alternatively, the collector plate 850 may remain stationary while the spinneret 820 and/or the target 860 move relative to the collector plate.

The relative movement of the collector plate 850 with respect to the spinneret 820 and/or the target 860 may influence several properties of the resulting coating of fibers. For example, moving the collector plate 850 at a higher speed relative to the spinneret 820 may cause a reduction in the thickness of the coating. This may be caused, for example, because a portion of the collector plate 850 may be disposed in the path of the cone 833 for a shorter period of time when the collector plate is moving at a higher speed. Moving the collector plate 850 at a higher speed relative to the spinneret 820 also may cause the fibers to be increasingly aligned with one another. This may affect the strength, resiliency, and porosity of the coating. Also for example, as the distance between the spinneret 820 and the collector plate 850 is increased, the solution stream 832 may be required to travel a greater distance before reaching the collector plate. This may affect the splaying and drying characteristics of the solution stream 832.

The collector plate 850 may be similar in many respects to the collector plate 750 described in reference to FIG. 7. For example, the collector plate 850 of FIG. 8 may be sized and shaped to correspond to a desired size and shape of a graft material for covering a prosthesis. The collector plate 850 also may include a plurality of openings to produce a graft material having a corresponding plurality of openings formed therein. An apparatus having a target that is independent of the collector plate may be beneficial in that removal and replacement of the collector plate from the apparatus may be relatively fast and efficient. This may allow a first collector plate with the coating or network of non-woven fibers formed thereon to be removed from the apparatus and replaced with a second collector plate so that the electrospinning process may be repeated on the second collector plate while the graft material is being removed from the first collector plate.

The collector plate 850 may be formed from a conductive material as described above. Alternatively, because the apparatus of FIG. 8 may include the charged target 860, the collector plate 850 may be formed from a non-conductive material. In other words, employing the charged target 860 to attract the charged solution stream 832 may make it unnecessary to form the collector plate 850 from a conductive material. The collector plate 850 may be formed from any suitable material including, for example, PVC, silicone, polyurethane, an insulating polymer, or a metal. The ability to form the collector plate 850 from a non-conductive material may be beneficial. For example, the collector plate 850 may be formed from a material that may easily release the coating of non-woven fibers intact, or undamaged, for use as the graft material of the prosthesis. One example of a material that may be suitable for easily releasing the coating of the graft material may be PTFE.

A graft material formed using an electrospinning process may include a plurality of continuous electrospun fibers. It may be expected that a majority of the electrospun fibers of the graft material may be continuous. However, due to aberrations or abnormalities which may occur during the manufacturing process or a subsequent handling process, the graft material also may include one or more severed fibers. For example, an electrospun fiber may be severed during relative movement between the spinneret and the collector plate as described above. Also for example, an electrospun fiber may be severed during removal of the graft material from the collector plate or during another processing step.

Figure 9A:
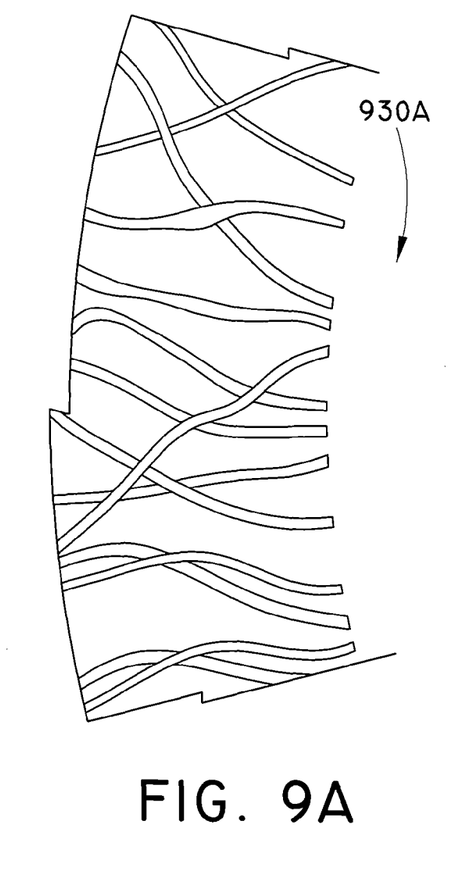
FIG. 9A illustrates a portion of an opening formed in an electrospun graft material by electrospinning.
Figure 9B:
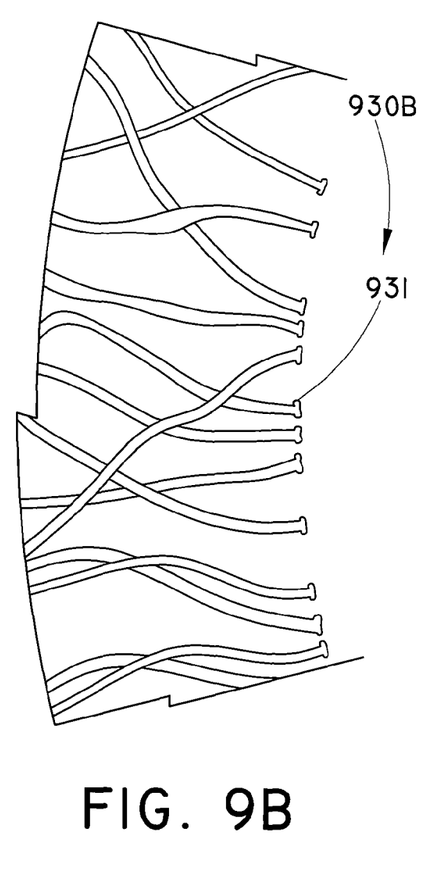
FIG. 9B illustrates a portion of an opening formed in an electrospun graft material by laser marking.
Figure 9C:
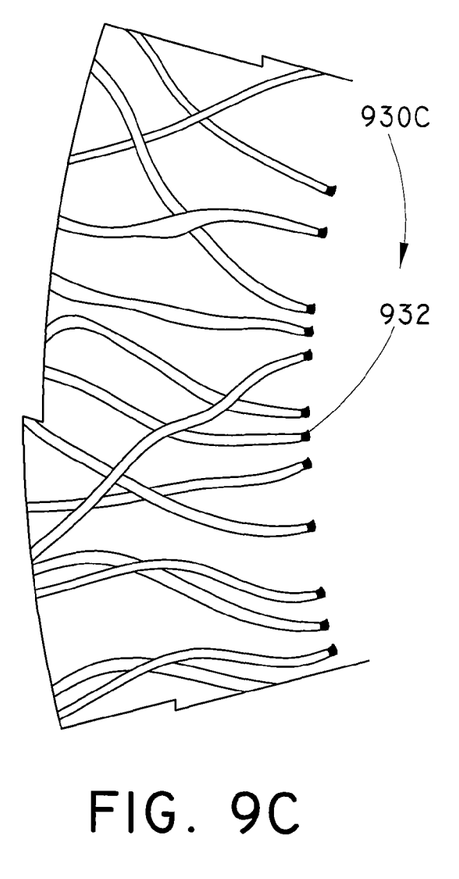
FIG. 9C illustrates a portion of an opening formed in an electrospun graft material by mechanical punching.
Figure 9D:
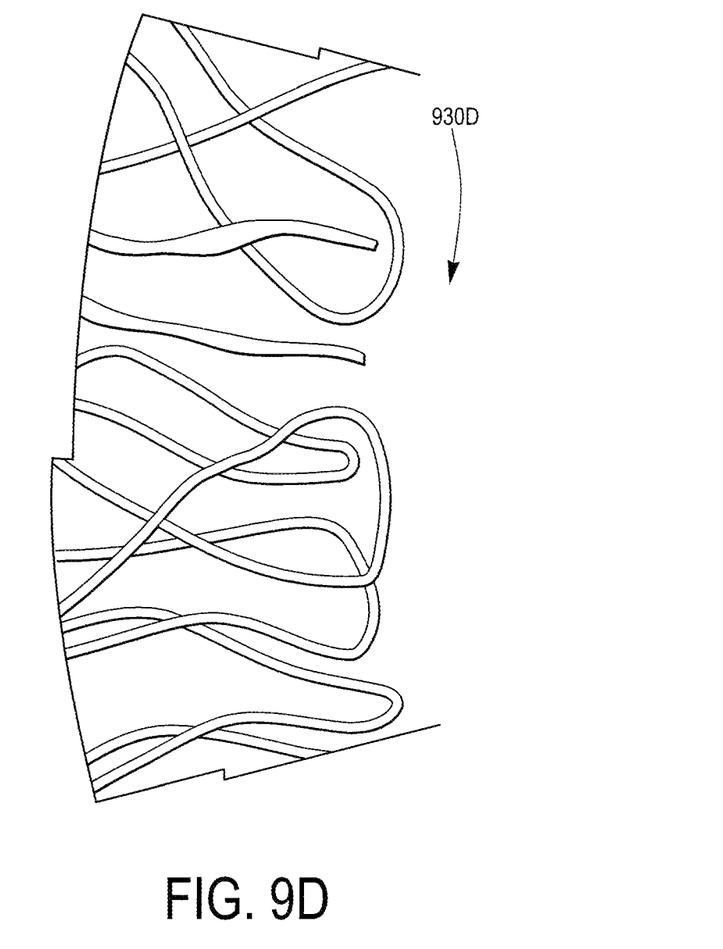
FIG. 9D illustrates a portion of an opening formed in an electrospun graft material by electrospinning in accordance with the invention.

Forming the patterned graft material using an electrospinning process may have multiple advantages. FIGS. 9A-9D show close-up views of portions of the edges of openings 930 formed in a network of electrospun fibers. The edge of each opening may be defined by one or more electrospun fibers of the network of electrospun fibers. FIGS. 9A and D shows an openings 930a and 930d formed by electrospinning; FIG. 9C shows an opening 930c formed by laser marking; and FIG. 9B shows an opening 930b formed by mechanical punching. Because openings may be precisely formed in the collector plate (e.g., by machining), the size and/or shape of each opening 930a and 930d formed by electrospinning may be precisely controlled. Additionally, the openings 930a and 930d of the electrospun patterned graft material may be homogeneous. Forming the openings 930c by laser marking in a subsequent processing step after formation of the graft material may burn or melt portions of the fibers surrounding the openings. Thus, an individual fiber of the graft material may include a burnt or melted end portion 932 along the edge of the opening 930c as shown in FIG. 9C. Forming openings by laser marking or mechanical punching in a subsequent processing step after formation of the graft material may sever individual fibers of the graft material surrounding the openings. Severing an individual fiber by laser marking may form a burnt or melted end portion 932 as described above. An individual fiber severed by mechanical punching may include a frayed end portion 931 along the edge of the opening 930b as shown in FIG. 9B. The burnt or melted end portion 932 and/or the frayed end portion 931 may form an irregular edge surrounding the opening 930 in the graft material. In contrast, an electrospun patterned graft material formed as described herein may be substantially free of burns, frayed edges, melted fibers, or severed fibers along the edges surrounding the openings in the graft material. The edges surrounding the openings formed in the network of electrospun fibers may be defined by one or more electrospun fibers, and a majority of the electrospun fibers defining the edges may be continuous at the edges as shown in 930d. The openings also may be substantially uniform. This may provide a graft material having a precisely controlled porosity.

Solutions for use in the electrospinning process of the present disclosure may include any suitable liquids containing materials to be electrospun. For example, solutions may include, but are not limited to, suspensions, emulsions, melts, and hydrated gels containing the materials, substances, or compounds to be electrospun. Solutions also may include solvents or other liquids or carrier molecules.

Appropriate materials for electrospinning may include any compound, molecule, substance, or group or combination thereof that may form any type of structure or group of structures during or after electrospinning. For example, materials may include natural materials, synthetic materials, or combinations thereof. Naturally occurring organic materials may include any substances naturally found in the body of plants or other organisms, regardless of whether those materials have or can be produced or altered synthetically. Synthetic materials may include any materials prepared through any method of artificial synthesis, processing, or manufacture. In one example, the materials may be biologically compatible materials. Such materials may include, for example, any materials that may be used to form a graft material of a prosthesis as described above.

One class of materials for electrospinning may include extracellular matrix (ECM) materials. ECM materials may include, for example, collagen, fibrin, elastin, laminin, and fibronectin. In one example, the material may include collagen of any type. Additional materials may include further ECM components, for example, proteoglycans.

In one example, the solution may include synthetic materials, such as biologically compatible synthetic materials. Synthetic materials may include polymers such as, for example, poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolid-es) (PLGA), polyanhydrides, polyorthoesters or any other similar synthetic polymers that may be developed that are biologically compatible. Biologically compatible synthetic polymers also may include copolymers, blends, or any other combinations of the forgoing materials either together or with other polymers generally. The use of these polymers will depend on given applications and specifications required. Suitable polymer material may include, for example, polyester such as DACRON™, polyetherurethanes such as THORALON® from Thoratec Corporation (Pleasanton, Calif.), or polyethylene terephthalate (PET).

Solutions may include any solvent that allows delivery of the material or substance to the orifice, tip of a syringe, or other site from which the material may be electrospun. The solvent may be used for dissolving or suspending the material or the substance to be electrospun. For example, solvents for use in electrospinning may create a mixture with collagen and/or other materials to be electrospun, to enable electrospinning of such materials. Suitable solvents may include, for example, trifluoroacetic acid, dichloromethane, dimethylacetamide (DMAc), or any other suitable solvent.

The concentration of a given solvent may be an important consideration in electrospinning. Interactions between molecules of materials during electrospinning may stabilize the solution stream, leading to fiber formation. The solvent may sufficiently dissolve or disperse the polymer to prevent the solution stream from disintegrating into droplets, thereby enabling formation of a stable stream in the form of a fiber. In one example, the solution may have a concentration of about 0.005 g/mL to about 0.15 g/mL, about 0.01 g/mL to about 0.12 g/mL, or about 0.04 g/mL to about 0.09 g/mL.

Solvents that may be useful for dissolving or suspending a material or a substance may depend on the material or substance. For example, collagen may be electrospun as a solution or suspension in water, 2,2,2-trifluoroethanol, 1,1,1,3,3,3-hexafluoro-2-propanol (also known as hexafluoroisopropanol or HFIP), or combinations thereof. Fibrin monomer may be electrospun from solvents such as urea, monochloroacetic acid, water, 2,2,2-trifluoroethanol, HFIP, or combinations thereof. Elastin may be electrospun as a solution or suspension in water, 2,2,2-trifluoroethanol, isopropanol, HFIP, or combinations thereof, such as isopropanol and water.

Other lower order alcohols, especially halogenated alcohols, may be used as solvents. Other solvents may include, for example, acetamide, N-methylformamide, N,N-dimethylformamide (DMF), dimethylsulfoxide (DMSO), dimethylacetamide, N-methyl pyrrolidone (NMP), acetic acid, trifluoroacetic acid, ethyl acetate, acetonitrile, trifluoroacetic anhydride, 1,1,1-trifluoroacetone, maleic acid, hexafluoroacetone.

Proteins and peptides associated with membranes may be hydrophobic and thus may be substantially insoluble in aqueous solutions. Such proteins may be dissolved in organic solvents such as methanol, chloroform, and trifluoroethanol (TFE) and emulsifying agents. Any other solvents may be used such as, for example, solvents useful in chromatography, especially high performance liquid chromatography. Proteins and peptides also may be soluble in, for example, HFIP, hexafluoroacetone, chloroalcohols in conjugation with aqueous solutions of mineral acids, dimethylacetamide containing 5% lithium chloride, and in acids such as acetic acid, hydrochloric acid and formic acid. In some examples, the acids may be very dilute, while in other examples the acids may be concentrated. N-methyl morpholine-N-oxide may also be used as a solvent with many polypeptides. Other compounds, used either alone or in combination with organic acids or salts, that may be used as solvents include, for example, triethanolamine; dichloromethane; methylene chloride, 1,4-dioxane, acetonitrile, ethylene glycol, diethylene glycol, ethyl acetate, glycerine, propane-1,3-diol, furan, tetrahydrofuran, indole, piperazine, pyrrole, pyrrolidone, 2-pyrrolidone, pyridine, quinoline, tetrahydroquinoline, pyrazole, and imidazole. Combinations of solvents may also be used.

Synthetic polymers may be electrospun using solvents such as, for example, HFIP, methylene chloride, ethyl acetate, acetone, 2-butanone (methyl ethyl ketone), diethyl ether, ethanol, cyclohexane, water, dichloromethane (methylene chloride), tetrahydrofuran, dimethylsulfoxide (DMSO), acetonitrile, methyl formate, and various solvent mixtures. HFIP and methylene chloride may be desirable solvents.

Selection of a solvent may depend upon the characteristics of the synthetic polymer to be electrospun. Selection of a solvent may be based, for example, on consideration of secondary forces that may stabilize polymer-polymer interactions and the solvent's ability to replace these secondary forces with strong polymer-solvent interactions. In the case of polypeptides such as collagen, and in the absence of covalent crosslinking, the principal secondary forces between chains may be: (1) coulombic, resulting from attraction of fixed charges on the backbone and dictated by the primary structure (e.g., lysine and arginine residues may be positively charged at physiological pH, while aspartic or glutamic acid residues may be negatively charged); (2) dipole-dipole, resulting from interactions of permanent dipoles (the hydrogen bond, commonly found in polypeptides, may be the strongest of such interactions); and (3) hydrophobic interactions, resulting from association of non-polar regions of the polypeptide due to a low tendency of non-polar species to interact favorably with polar water molecules. Solvents or solvent combinations that may favorably compete for these interactions may dissolve or disperse polypeptides. For example, HFIP and TFE may possess a highly polar OH bond adjacent to a very hydrophobic fluorinated region. Additionally, the hydrophobic portions of these solvents may interact with hydrophobic domains in polypeptides, helping to resist the tendency of the latter to aggregate via hydrophobic interactions. In some examples, solvents may be selected based on their tendency to induce helical structure in electrospun protein fibers, thereby predisposing monomers of collagen or other proteins to undergo polymerization and form helical polymers that mimic the native collagen fibril. Examples of such solvents may include halogenated alcohols, preferably fluorinated alcohols (HFIP and TFE), hexafluoroacetone, chloroalcohols in conjugation with aqueous solutions of mineral acids, and dimethylacetamide, preferably containing lithium chloride. HFIP and TFE may be especially preferred. In some examples, water may be added to the solvents.

The, solvent also may have a relatively high vapor pressure to promote the stabilization of an electrospinning solution stream to create a fiber as the solvent evaporates. In examples involving higher boiling point solvents, it may be desirable to facilitate solvent evaporation by warming the spinning solution, and optionally the solution stream itself, or by electrospinning in reduced atmospheric pressure.

Solutions also may include one or more bioactive agents. A therapeutically effective amount of a bioactive agent by be incorporated into the graft material produced by the electrospinning process for implantation within a patient. The bioactive agent may be selected to perform a desired function upon implantation. For example, the bioactive agent may be selected to treat indications such as atherosclerosis, renal dialysis fistulae stenosis, or vascular graft stenosis. A graft material including a bioactive agent may be useful when performing procedures such as coronary artery angioplasty, renal artery angioplasty, or carotid artery surgery. Also for example, a bioactive agent such as a growth factor may be selected to promote ingrowth of tissue from the interior wall of a body vessel. An anti-angiogenic or antineoplastic bioactive agent such as paclitaxel, sirolimus, or a rapamycin analog, or a metalloproteinase inhibitor such as batimastaat may be included to mitigate or prevent undesired conditions in the vessel wall, such as restenosis. Many other types of bioactive agents also may be included in the solution.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A patterned graft material comprising:
   a network of electrospun fibers comprising a plurality of continuous electrospun fibers; and
   a plurality of openings in the network of electrospun fibers, the plurality of openings arranged in a pattern;
   wherein the network of electrospun fibers comprises a plurality of edges each surrounding a corresponding one of the plurality of openings and including at least one electrospun fiber of the network of electrospun fibers, and a majority of the electrospun fibers of the plurality of edges are continuous at the edges, and
   wherein the network of fibers do not cross the plurality of openings.

2. The patterned graft material of claim 1, wherein the patterned graft material has a determined porosity, the porosity determined by a size of the openings in the network of electrospun fibers.

3. The patterned graft material of claim 1, wherein the patterned graft material has a determined porosity, the porosity determined by a number of openings in the network of electrospun fibers.

4. The patterned graft material of claim 1, wherein the patterned graft material has a determined porosity, the porosity determined by the pattern of the plurality of openings in the network of electrospun fibers.

5. The patterned graft material of claim 1, further comprising at least a first region and a second region, the first region having a first determined porosity and the second region having a second determined porosity different from the first determined porosity.

6. The patterned graft material of claim 5, wherein the first and second regions are positioned adjacent to one another along a length of the patterned graft material.

7. The patterned graft material of claim 5, wherein at least one of the first and second regions is substantially nonporous.

8. The patterned graft material of claim 1, wherein the edge surrounding each of the plurality of openings is substantially free of severed fibers and melted fibers.

* * * * *